(12) United States Patent
Yano et al.

(10) Patent No.: US 9,097,690 B2
(45) Date of Patent: Aug. 4, 2015

(54) SAMPLE PREPROCESSING AND CONVEYING SYSTEM

(75) Inventors: Shigeru Yano, Hitachinaka (JP); Atsushi Suzuki, Naka (JP); Yasushi Aoki, Hitachinaka (JP); Tatsuya Fukugaki, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 665 days.

(21) Appl. No.: 13/388,813

(22) PCT Filed: Sep. 17, 2010

(86) PCT No.: PCT/JP2010/005672
§ 371 (c)(1),
(2), (4) Date: Feb. 29, 2012

(87) PCT Pub. No.: WO2011/039965
PCT Pub. Date: Apr. 7, 2011

(65) Prior Publication Data
US 2012/0179405 A1 Jul. 12, 2012

(30) Foreign Application Priority Data

Sep. 30, 2009 (JP) ................................. 2009-225915

(51) Int. Cl.
*G01N 35/02* (2006.01)
*G01N 35/00* (2006.01)

(52) U.S. Cl.
CPC ............ *G01N 35/02* (2013.01); *G01N 35/0092* (2013.01)

(58) Field of Classification Search
USPC .......... 702/85; 73/863.01, 863.92; 422/64, 65
See application file for complete search history.

(56) References Cited

U.S. PATENT DOCUMENTS

| 5,902,549 A | 5/1999 | Mimura et al. |
| 6,290,907 B1 * | 9/2001 | Takahashi et al. ............. 422/65 |

(Continued)

FOREIGN PATENT DOCUMENTS

| JP | 09-043246 A | 2/1997 |
| JP | 09-243646 A | 9/1997 |

(Continued)

OTHER PUBLICATIONS

Japanese Office Action received in Japanese Application No. 2011-534055 dated Dec. 10, 2013.

(Continued)

*Primary Examiner* — John Breene
*Assistant Examiner* — Hien Vo
(74) *Attorney, Agent, or Firm* — Mattingly & Malur, PC

(57) ABSTRACT

In a large-scale analyzing system arrangement with a multi-sample processing capability, connecting a plurality of analyzing systems each having a minimum analyzer configuration makes it difficult for each analyzing system to continue analysis while managing and sharing the consumables information required for measurement between the analyzers. Additionally, since the sample preprocessing and conveying system does not recognize operational states of the analyzing systems during the analysis, conveyance of the sample to an analyzing system unable to conduct the analysis is likely to occur, resulting in delays in reporting the test results on the sample. The internal operational status of a plurality of analyzing systems is collectively managed and samples are conveyed between the analyzing systems. If the analysis is determined not to be capable of being continued, the sample is temporarily placed in a stand-by condition and then the analysis, after returning to a restartable state, is automatically continued.

6 Claims, 3 Drawing Sheets

(56) References Cited

U.S. PATENT DOCUMENTS

| | | |
|---|---|---|
| 2002/0015665 A1 | 2/2002 | Lindsey et al. |
| 2008/0069730 A1 | 3/2008 | Itoh |

FOREIGN PATENT DOCUMENTS

| | | |
|---|---|---|
| JP | 10-282106 A | 10/1998 |
| JP | 11-223634 A | 8/1999 |
| JP | 2988362 B2 | 10/1999 |
| JP | 2004-061169 A | 2/2004 |
| JP | 2004-505249 A | 2/2004 |
| JP | 2008-076185 A | 4/2008 |
| JP | 2009-008558 A | 1/2009 |

OTHER PUBLICATIONS

Japanese Office Action received in corresponding Japanese Application No. 2011-534055 dated Feb. 14, 2014.

* cited by examiner

SAMPLE PREPROCESSING AND CONVEYING SYSTEM

TECHNICAL FIELD

The present invention relates to a sample conveying scheme and sample handling method intended to improve measuring efficiency of analyzers in a sample preprocessing and conveying system to which analyzing systems are connected.

BACKGROUND ART

As with the invention described in Patent Document 1, a large-scale analyzing system with a multi-sample processing capability includes main conveyance lines for conveying samples, and a plurality of analyzers arranged along the main conveyance lines and each equipped with analytical reaction units, sample dispensing units for dispensing a sample into dispensed samples for the analytical reaction units, and reagent supply units for supplying to each reaction unit a reagent corresponding to an analysis item. In the analyzing system that collectively analyzes multiple samples using the analyzers, the reagent to be used for measuring one kind of analysis item is supplied to each of the analyzers for the system to determine whether the quantity of corresponding reagent in one analyzer is sufficient.

In the case where a reagent is insufficient, the system conveys the corresponding sample to another analyzer possessing the reagent, and this analyzer conducts the sample. This sequence has enabled clinical or laboratory tests without causing a stoppage of any analyzers due to an insufficiency of a reagent, and thus contributed to rapid reporting of test results.

In sample preprocessing and conveying systems each with a plurality of automatic analyzers connected thereto, sample conveyance destinations are determined by parameterizing measurement items and processing capabilities of the automatic analyzers from load states of the automatic analyzers and a congestion status of conveyance lines so that measurement results can be obtained earlier.

PRIOR ART LITERATURE

Patent Documents

Patent Document 1: Japanese Patent No. 2988362

SUMMARY OF THE INVENTION

Problems to be Solved by the Invention

However, cases of installing a sample preprocessing and conveying system including, instead of one analyzing system with a plurality of analyzers, a plurality of analyzing systems each of a minimal configuration, for example with one analyzer, have increased with the improvement of throughput in analyzers capable of processing multiple samples collectively.

Such a tendency makes it difficult to apply a function that allows the plurality of analyzers in each analyzing system to continue analysis while managing and sharing the consumables information required for measurement between the analyzers. Additionally, since the sample preprocessing and conveying system does not recognize operational states of the analyzing systems during the analysis, conveyance of the sample to an analyzing system unable to conduct the analysis is likely to happen and if this actually occurs, reporting test results on the sample will be delayed.

Furthermore, current sample preprocessing and conveying systems calculate a load status of analyzing systems from a congestion status of buffers connected to the analyzing systems. However, there may arise a situation under which the analyzing systems should not use only the buffer load status.

For example, during calibration measurement with an analyzing system, until the analyzing system has later become operable for analysis, there is a need for an operator to control the sample preprocessing and conveying system by taking an appropriate action such as avoiding the conveyance of the sample from the sample preprocessing and conveying system or bringing this system to a temporary stop. A better-suited conveyance destination is therefore determined by obtaining and assessing data on operational states including the type of sample being measured with the analyzing system.

Means for Solving the Problems

The present invention continues analysis by collectively managing an internal operational status of a plurality of analyzing systems and conveying a sample between the analyzing systems in a cross-sectional way. If the analysis is determined not to be capable of being continued, the sample is temporarily placed in a stand-by condition and then the analysis, after returning to a restartable state, is automatically continued using the sample, to reduce an operator's manual processing.

Effects of the Invention

In accordance with the present invention, information on reagents, diluting agents, reaction vessels, and other consumable materials required for measurement, can be obtained by collectively managing an operational status of a plurality of analyzing systems and linking this collective management to conveyance management of samples. An unmeasurable state of the analyzing systems, a partial stoppage thereof due to hardware errors, and a discontinuation of analysis on an item-by-item or sample-by-sample basis are also avoided. Furthermore, An operator load can be reduced by automating sample reloading.

BEST MODE FOR CARRYING OUT THE INVENTION

Figure 1:
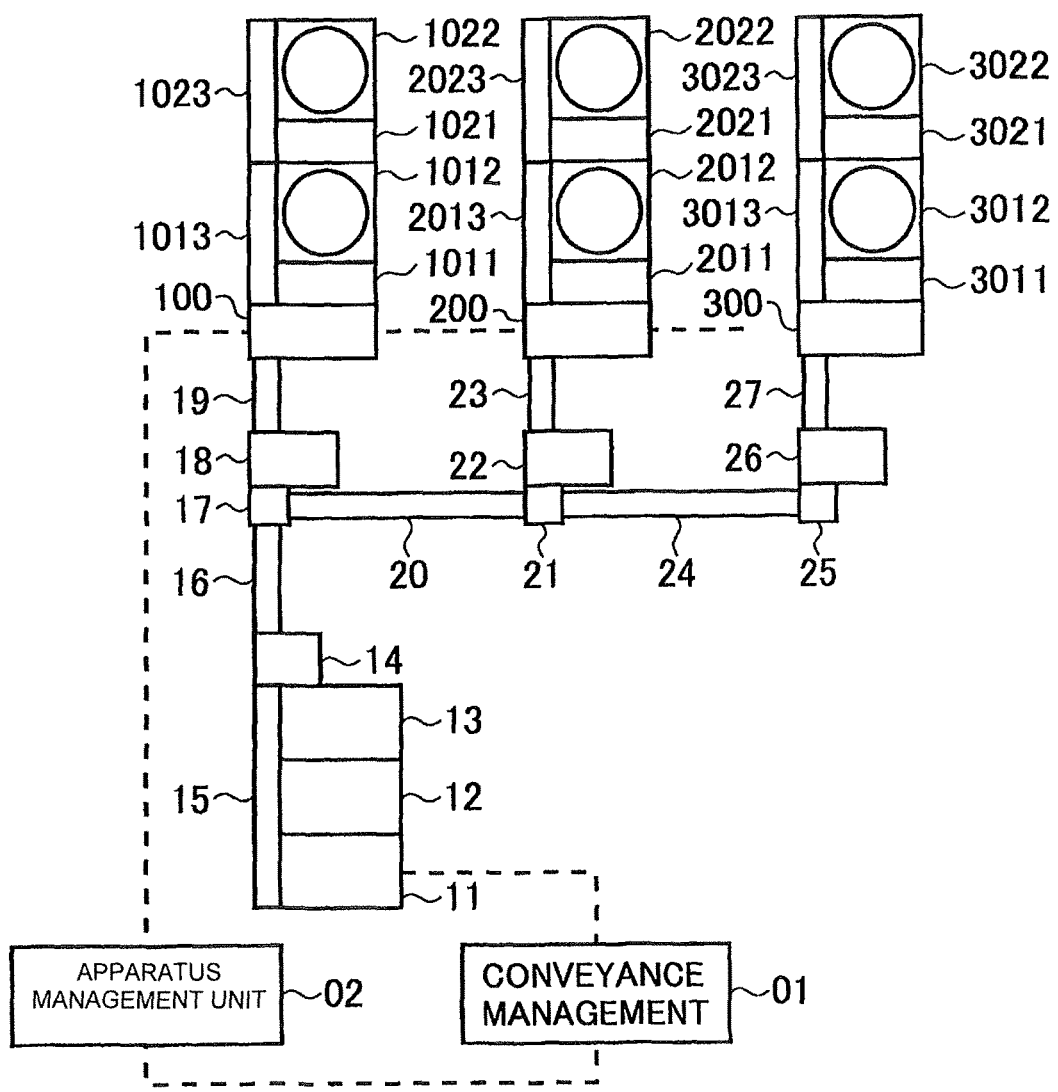
FIG. 1 is a system layout diagram of a sample preprocessing and conveying system with analyzing systems connected thereto.
Figure 2:
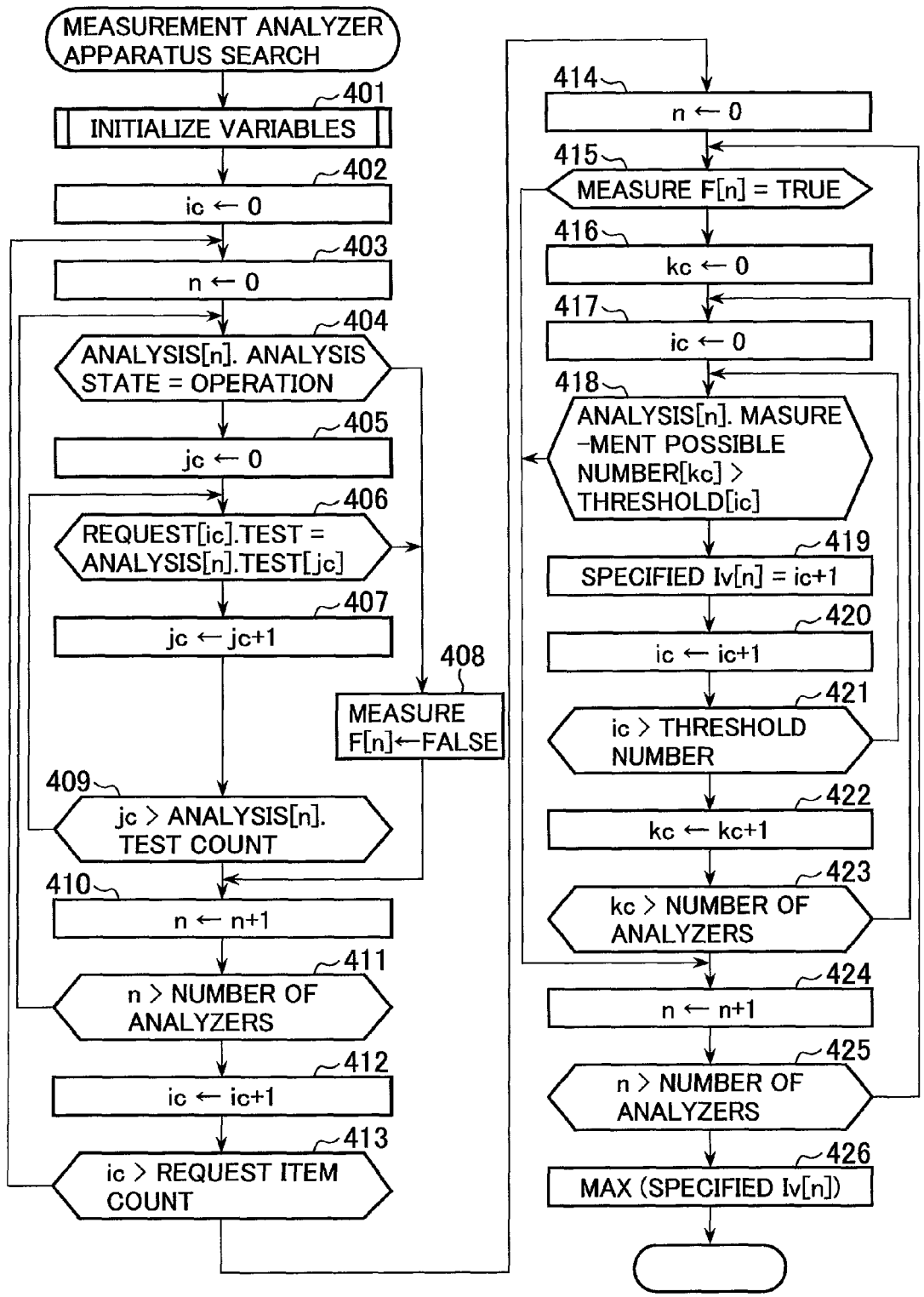
FIG. 2 is a process flow of operational status determination by a conveyance management unit 01.
Figure 3:
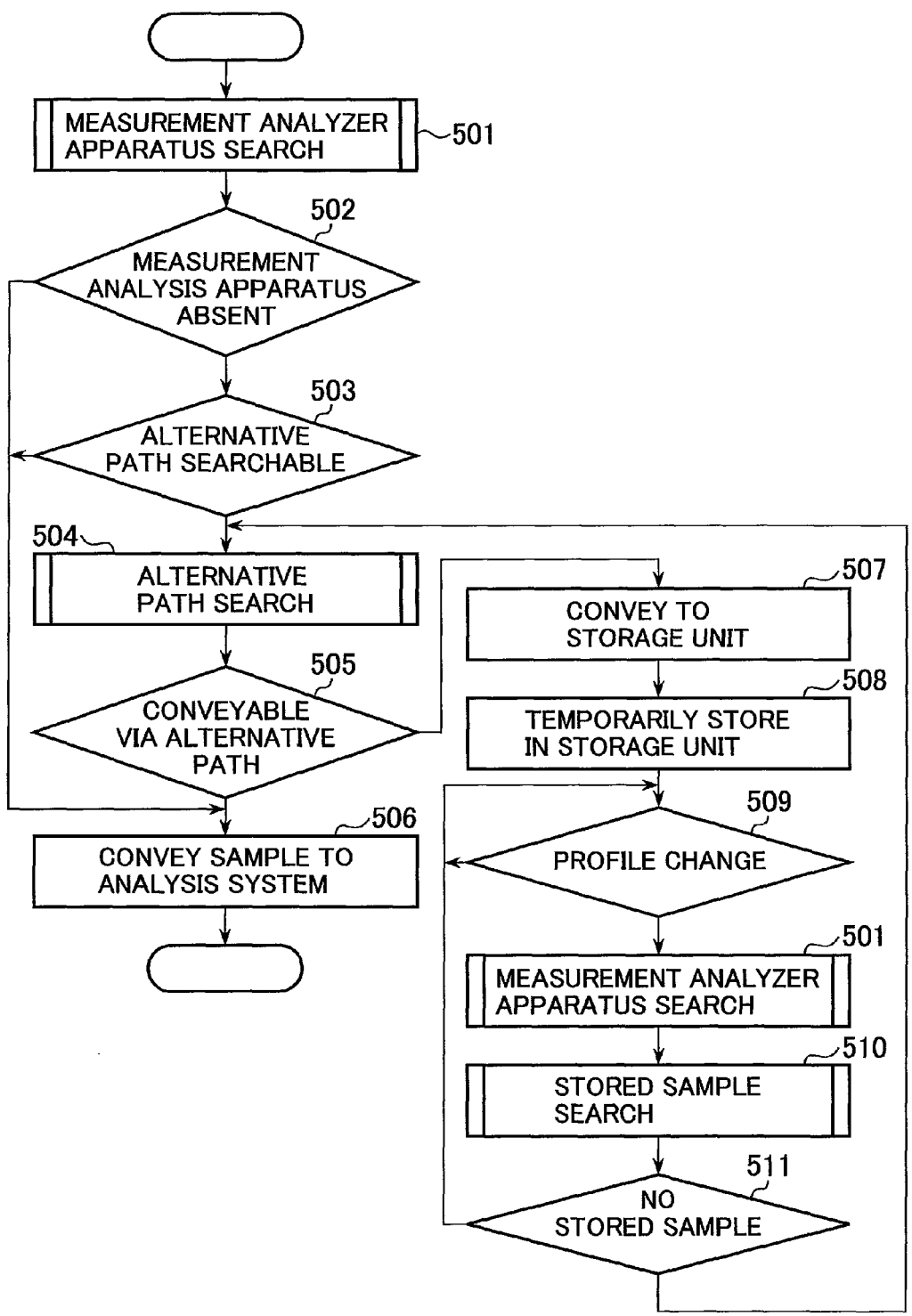
FIG. 3 is a process flow of a conveyance destination change by the conveyance management unit 01.

FIG. 1 shows an example of interconnecting a sample preprocessing and conveying system and a plurality of analyzing systems. The sample preprocessing and conveying system is connected to the analyzing systems 100, 200 and 300. One kind of item-specific reagent is placed in an appropriate form at an analyzer 1012 of the analyzing system 100 and an analyzer 2012 of the analyzing system 200, and a sample loading unit 14 confirms clinical or laboratory test items of each sample that are to be measured, and states of buffers 18 and 22. The sample preprocessing and conveying system thereby determines whether the sample is to be conveyed to the analyzing system 100 or the analyzing system 200. In addition, specified kinds of item-specific reagents are placed appropriately at the analyzing system 300, and similarly to the above, samples to be measured with the analyzing system 300 are conveyed thereto. The analyzing systems 100, 200 and 300 notify their own states to an apparatus management unit 20, by communication or other means, thus the apparatus management unit 02 is to have such an analyzing system status management table as in Table 1. The apparatus management unit 02, by continuously monitoring the analyzing system status management table, transmits such analysis-measurable state information (a state profile) as in Table 3, to a conveyance management unit 01. The conveyance management unit 01 refers to such a pre-registered analytical load threshold data table as in Table 2 and determines conveyance destinations of the samples from the analysis-measurable state information that denotes analysis states, the number of samples of each type, and the number of tests. Appropriate data is set as analytical load threshold data according to an operational status of the loading destination system, or the analytical load threshold data is automatically corrected to ensure an operating load balance between the distributed systems.

In a desirable embodiment of the present invention, the apparatus management unit 02 detects insufficiency of the item-specific reagent, one of the consumables required for the measurement of the corresponding item, in the analyzer 1012 of the analyzing system 100, and determines that the sample including the particular item can be measured with the analyzer 2012 of the analyzing system 200. The apparatus management unit 02 also instructs the analyzing system 100 to return the sample from the analyzer 1012 to a conveyance line 19, and at the same time, sends the analysis-measurable state information of Table 3 to the conveyance management unit 01. In addition, the apparatus management unit 02, upon determining the sample to be measurable with the analyzer 2012 of the analyzing system 200, notifies to the conveyance management unit 01 that the analyzer 2012 is the apparatus to analyze the sample. Next, the conveyance management unit 01 views the analysis-measurable state information of Table 3, recognize that the destination of the sample which has been returned to the conveyance line 19 is the analyzing system 200, and conveys the sample to the analyzing system 200, which then measures the item. Furthermore, the apparatus management unit 02 conducts management so that all samples loaded from sample loading units 11, 14 and corresponding to a particular test request item, that is, the item for which the shortage of reagent has been detected, are conveyed to the analyzing system 200.

In another desirable embodiment of the present invention, the conveyance management unit 01 calculates a list of samples queuing in the buffers 18, 22 and 26 thereafter notifies calculation results to the apparatus management unit 02. The apparatus management unit 02 conducts comparisons between a total number of analysis items corresponding to the analysis-queued samples in Table 1, and useable consumables volumes required for measurement. Upon determining either of the consumables to be insufficient in quantity, the apparatus management unit 02 sends to the conveyance management unit 01 the analysis-measurable state information of Table 3 that indicates the facts that the insufficiency has been determined and thus that the analysis with the analyzing system has become unable to be continued. The conveyance destination can also be changed as a result.

In the preprocessing and conveying system, the analyzing systems 100 and 200 usually conduct measurements relating to the same item, and generally convey samples in alternate manner. Accordingly, the quantity of consumables consumed in the analyzing system 100 and that of the analyzing system 200 become much the same level, so for example, the reagent corresponding to the same item is most likely to run short at the same time of the day between the analyzing systems 100 and 200. At this time, the apparatus management unit 02 detects from the analyzing system status management table the fact that the reagent corresponding to the particular item has run short in all analyzers useable for the measurement, and sends to the conveyance management unit 01 the analysis-measurable state information of Table 3 that indicates the fact that the analysis of the item is unable to be continued. The conveyance management unit 01 then makes the sample stand by in a sample storage unit 13.

After this, if the item becomes measurable with the analyzing system 100 or 200, the apparatus management unit 02 detects from the analyzing system status management table that the measurement with the analyzing system 100 or 200 has become possible, and notifies the analyzing system that has become useable for the measurement, to the conveyance management unit 01. The conveyance management unit 01 then automatically extracts the corresponding sample from the sample storage unit 13 and conveys the sample to the analyzing system 100 or 200, for analysis of the unmeasured item.

In addition, if a dispensing machine 12 for creating child samples from a parent sample is creating the child samples to be conveyed to the analyzing system 100, 200, the conveyance management unit 01 upon finding that the analysis of the item has become unable to be continued can stop the creation of further child samples by making the parent sample stand by in the sample storage unit 13. After this, when the item becomes measurable with the analyzing system 100 or 200, the conveyance management unit 01 extracts the parent sample from the sample storage unit 13 automatically and conveys the parent sample to the dispensing machine 12. This enables the dispensing machine 12 to restart creating child samples and convey these child samples to the analyzing system 100 or 200. Thus, the unmeasured item can be analyzed.

In addition to reagent information, the analyzing system status management table shown in Table 1 contains information on the number of samples retained by the analyzing systems, so the apparatus management unit 02 can comprehend the operational status of each analyzing system and the kinds of samples currently undergoing processing. When the analyzing system is measuring a specific kind of sample, the apparatus management unit 02 can notify to the conveyance management unit 01 that the analysis with that analyzing system is impossible. Thus, for example if the analyzing system is under calibration, the apparatus management unit 02 can notify to the conveyance management unit 01 that the analysis with the particular analyzing system cannot be continued. The conveyance management unit 01 can therefore cause the sample to stand by in the buffer in front of the analyzing system until the analyzing system has become operable for analysis once again, or if the buffer is likely to become full, the sample preprocessing system can suspend accepting new samples from the sample loading unit 11, 14. In the latter case, the sample preprocessing system can instead operate appropriately according to the particular operational status of the analyzing system and determine operation of a preprocessing unit.

If the analysis state of the analyzing system, shown in Table 1, is "Maintenance", the apparatus management unit 02 determines that the sample cannot be conveyed to that analyzing system, and notifies to the conveyance management unit 01 that the particular analyzing system has become unable to continue the analysis. The conveyance management unit 01 consequently becomes able to select a conveyance destination other than the analyzing system of interest. Furthermore, if the sample is an urgent sample the test items of which include one analyzable only by the analyzing system whose analysis state is "Maintenance", the conveyance management unit 01 can assign the analysis of that sample to an offline urgent-sample analyzer, in which case, the conveyance management unit 01 activates the dispensing machine 12 to create and dispense child samples, and then unloads the dispensed child samples into the sample storage unit 13. This enables an operator to obtain the child samples to be analyzed, without waiting for a recovery of the analyzing system from the maintenance state. In addition, the obtained child samples can be loaded into the urgent-sample analyzer or the like and test results can be reported rapidly.

TABLE 1

|  |  | 1st analyzing system | 2nd analyzing system | 3rd analyzing system |
|---|---|---|---|---|
| Analysis state |  | Operation | Operation | Maintenance |
| Retained samples | Non-urgent | 34 | 0 | 0 |
|  | Urgent | 3 | 0 | 0 |
|  | QC | 3 | 0 | 0 |
|  | Calib | 0 | 4 | 0 |
| Consumables | Reaction vessel | 277 | 391 |  |
|  | Diluting agent | 200 | 221 | 110 |
| Useable reagent | Test 01 | 332 | 365 |  |
|  | Test 02 | 226 | 224 |  |
|  | Test 03 | 2 | 142 |  |
|  | Test 04 | 1107 | 122 |  |
|  | ... | ... | ... | ... |
|  | Test 21 |  |  | 77 |
|  | ... | ... | ... | ... |

TABLE 2

|  | 1st analyzing system | 2nd analyzing system | 3rd analyzing system |
|---|---|---|---|
| Threshold value [0] | 20 | 20 | 30 |
| Threshold value [1] | 50 | 50 | 60 |
| Threshold value [2] | 120 | 120 | 150 |

TABLE 3

|  | 1st analyzing system | 2nd analyzing system | 3rd analyzing system |
|---|---|---|---|
| Analysis state | Operation | Operation | Maintenance |
| Sample type 1 | 120 | 500 | 500 |
| Sample type 2 | 20 | 100 | 60 |
| Sample type 3 | 30 | 310 | 420 |
| Sample type 4 | 500 | 500 | 500 |
| Sample type 5 | 500 | 500 | 500 |
| Test 01 | 277 | 365 | 0 |
| Test 02 | 226 | 224 | 0 |
| Test 03 | 2 | 142 | 0 |
| Test 04 | 227 | 122 | 0 |
| ... | ... | ... | ... |
| Test 21 | 227 | 130 | 0 |

TABLE 3-continued

|  | 1st analyzing system | 2nd analyzing system | 3rd analyzing system |
|---|---|---|---|
| Test 22 | 0 | 0 | 0 |
| ... | ... | ... | ... |

Furthermore, in accordance with appended claim 5, the number of samples queued in the buffers positioned upstream with respect to the analyzing systems, and the number of processed samples in these buffers are recorded at time periods, as shown in Table 4. Applying an increment/decrement in the number of processed samples within the buffers to a method of least squares yields "$y=ax+b$" as a regression line function of the number of processed samples, where "a" becomes an index indicating whether the amount of sample to be conveyed from the sample preprocessing and conveying system to the analyzing system was processed at nearly predicted time of the day by the analyzing system. More specifically, if the index takes a negative value, it can be determined that the throughput of the analyzing system is of a level at which the amount of sample to be conveyed remains unprocessed. The regression line function can therefore be used to estimate a load of the analyzing system considering the number of samples queued in the buffers.

TABLE 4

|  | 1st sample buffer | | 2nd sample buffer | | 3rd sample buffer | |
|---|---|---|---|---|---|---|
|  | Queued samples | Processed samples | Queued samples | Processed samples | Queued samples | Processed samples |
| 060 | 12 | 4 | 9 | 2 | 5 | 3 |
| 120 | 11 | 5 | 8 | 2 | 5 | 3 |
| 180 | 11 | 4 | 9 | 2 | 4 | 2 |
| 240 | 12 | 5 | 9 | 2 | 5 | 3 |
| 300 | 13 | 5 | 8 | 3 | 4 | 3 |
| 360 | 13 | 5 | 8 | 3 | 4 | 2 |
| 420 | 14 | 4 | 8 | 3 | 3 | 2 |
| 480 | 15 | 4 | 9 | 5 | 4 | 2 |
| 540 | 16 | 5 | 10 | 5 | 5 | 2 |
| 600 | 16 | 5 | 10 | 5 | 4 | 3 |
| ... | ... | ... | ... | ... | ... | ... |

Under a situation that information on the operational status of the analyzing system is unobtainable therefrom, while automatic retest requests occurring in each analyzing system, urgent direct loading of samples into the analyzing systems, and other events that the sample preprocessing and conveying system connected to the analyzing systems cannot detect are being predicted, any analyzing system capable of obtaining test results within a shorter time can be determined as the apparatus to which the sample is to be conveyed.

DESCRIPTION OF REFERENCE NUMBERS

01 Conveyance management unit
02 Apparatus management unit
11, 14 Sample loading units
12 Dispensing machine
13 Sample storage unit
16, 19, 20, 23, 24, 27 Conveyance lines
17, 21, 25 Rotating units
18, 22, 26 Buffers
100, 200, 300 Analyzing systems

1011, 1021, 2011, 2021, 3011, 3021 Analyzer buffers
1012, 1022, 2012, 2022, 3012, 3022 Analytical reaction units
1013, 1023, 2013, 2023, 3013, 3023 Main conveyance lines of analyzing systems

The invention claimed is:

1. A sample preprocessing and conveying system, comprising:
    a plurality of conveyance lines to convey one or more sample carriers each constructed so that one or more sample containers are mounted thereon;
    a preprocessing system including a plurality of preprocessing units each arranged along one of the conveyance lines, the preprocessing units including a sample storage unit to store the sample carrier;
    a plurality of buffers, each to temporarily accept the sample carrier from the preprocessing units via the conveyance lines;
    a plurality of analyzing systems, each arranged downstream with respect to one of the buffers;
    a conveyance management unit to manage a conveyance destination of each sample carrier as one of the analyzing systems, and to control the preprocessing system and the conveyance lines; and
    an apparatus management unit to conduct integrated management of information on the analyzing systems, including criteria for determining whether measurement by each of the analyzing systems is possible,
    wherein the conveyance management unit is configured to control the preprocessing system and conveyance lines to:
    store the sample carrier in the sample storage unit temporarily when an analysis process of one of the analyzing systems transits to an analysis impossible condition, and
    extract the sample carrier temporarily stored in the sample storage unit and convey the sample carrier to the one of the analyzing systems when the analysis process of the one of the analyzing systems transits to an analysis possible condition.

2. The sample preprocessing and conveying system according to claim 1, wherein:
    the conveyance management unit transmits information on a queue size in each of the buffers to the apparatus management unit, and
    the apparatus management unit determines whether measurement by each of the analyzing systems is possible based on the information on the queue size in each of the buffers, and notifies the conveyance management unit when measurement by one of the analyzing systems is impossible.

3. The sample preprocessing and conveying system according to claim 1, wherein
    the conveyance management unit controls the conveyance lines and the buffers to store the sample carrier into one of the buffers automatically in accordance with whether measurement by the analyzing systems is possible.

4. The sample preprocessing and conveying system according to claim 3, wherein the sample carrier that has been stored into one of the buffers is removed, and the conveyance management unit determines another conveyance destination for the sample carrier.

5. The sample preprocessing and conveying system according to claim 1, wherein the analyzing systems are connected to the buffers and the preprocessing system by the conveyance lines,
    wherein the apparatus management unit periodically records a queue size of each of the, and notifies the conveyance management unit to convey the sample carrier to one of the buffers downstream from one of the analyzing systems based on the queue size of each of the buffers.

6. The sample preprocessing and conveying system according to claim 1, wherein the conveyance management unit is configured to control the preprocessing system and conveyance lines to:
    extract the sample carrier temporarily stored in the sample storage unit and convey the sample carrier to another one of the analyzing systems when the analysis process of the one of the analyzing systems remains in the analysis impossible condition.

* * * * *